(12) United States Patent
Chen (10) Patent No.: US 8,961,454 B2
(45) Date of Patent: Feb. 24, 2015

(54) MILK EXPRESSING DEVICE CAPABLE OF SIMULATING A BABY'S SUCKLING

(76) Inventor: Chean-Shui Chen, Taipei (TW)

( * ) Notice: Subject to any disclaimer, the term of this patent is extended or adjusted under 35 U.S.C. 154(b) by 0 days.

(21) Appl. No.: 13/556,214

(22) Filed: Jul. 24, 2012

(65) Prior Publication Data

US 2014/0031744 A1    Jan. 30, 2014

(51) Int. Cl.
*A61M 1/06*     (2006.01)
*A61M 1/00*     (2006.01)

(52) U.S. Cl.
CPC .............. *A61M 1/06* (2013.01); *A61M 1/066* (2014.02); *A61M 1/0031* (2013.01); *A61M 2205/3351* (2013.01)
USPC .............................................. 604/73; 604/74

(58) Field of Classification Search
CPC .... A61M 1/06; A61M 1/0011; A61M 1/0037
USPC ....................................................... 604/73, 74
See application file for complete search history.

(56) References Cited

U.S. PATENT DOCUMENTS

| | | | | |
|---|---|---|---|---|
| 4,795,428 A * | 1/1989 | Hwang | | 604/73 |
| 4,961,726 A * | 10/1990 | Richter | | 604/74 |
| 5,419,768 A * | 5/1995 | Kayser | | 604/119 |
| 5,520,652 A * | 5/1996 | Peterson | | 604/119 |
| 6,090,065 A * | 7/2000 | Giles | | 604/74 |
| 6,663,587 B2 * | 12/2003 | Silver et al. | | 604/74 |
| 6,673,036 B1 * | 1/2004 | Britto | | 604/74 |
| 7,029,454 B2 * | 4/2006 | Watanabe | | 604/74 |
| 7,381,197 B2 * | 6/2008 | Kelly et al. | | 604/74 |
| 7,527,608 B2 * | 5/2009 | Mason | | 604/151 |
| 7,972,297 B2 * | 7/2011 | Bryan et al. | | 604/74 |
| 8,070,715 B2 * | 12/2011 | Quackenbush et al. | | 604/74 |
| 8,137,305 B2 * | 3/2012 | Kelly et al. | | 604/74 |
| 8,398,584 B2 * | 3/2013 | Britto | | 604/74 |
| 8,545,438 B2 * | 10/2013 | Kazazoglu et al. | | 604/74 |
| 2003/0191433 A1 * | 10/2003 | Prentiss | | 604/74 |
| 2003/0236491 A1 * | 12/2003 | McKendry et al. | | 604/74 |
| 2009/0099511 A1 * | 4/2009 | Sutrina et al. | | 604/74 |
| 2011/0071466 A1 * | 3/2011 | Silver et al. | | 604/74 |
| 2012/0109084 A1 * | 5/2012 | Blott et al. | | 604/319 |
| 2013/0053764 A1 * | 2/2013 | Jaeger-Waldau | | 604/74 |
| 2013/0165852 A1 * | 6/2013 | Jager-Waldau | | 604/74 |
| 2013/0267933 A1 * | 10/2013 | Felber | | 604/514 |

* cited by examiner

Primary Examiner — Scott Medway (57) ABSTRACT

A milk expressing device capable of simulating a baby's suckling includes first and second vacuum sources, a throttle hole, a solenoid relief valve, first and second tubes, a breast shield, and a control circuit board. The first tube connecting the first vacuum source and the breast shield is provided with the throttle hole to communicate with the atmosphere. When the first vacuum source is turned off, negative pressure in the first tube and the breast shield disappears slowly through the throttle hole. The second tube connecting the second vacuum source and the breast shield is provided with the solenoid relief valve to communicate with the atmosphere. When the solenoid relief valve is activated, negative pressure in the second tube and in the breast shield is rapidly removed. The control circuit board controls the first and second vacuum sources and the solenoid relief valve.

2 Claims, 9 Drawing Sheets

FIG. 9

MILK EXPRESSING DEVICE CAPABLE OF SIMULATING A BABY'S SUCKLING

BACKGROUND OF THE INVENTION

1. Technical Field

The present invention relates to the technical field of babies' products. More particularly, the present invention relates to a milk expressing device which can simulate a baby's suckling.

2. Description of Related Art

Studies show that the feelings of a lactating mother have a significant influence on her milk production. Some positive examples of such feelings are a mother's profound fondness of her newborn, the thought of her baby's cuteness, and the belief that her milk is best for the baby. All these positive feelings are conducive to the secretion of milk. Some physical sensations such as touching or seeing the baby or hearing the baby cry also contribute to the reflex of milk secretion.

Therefore, a mother needs to be alongside her baby all the time so as to be able to look attentively at, caress, and respond to the baby. Being in close proximity to the baby also prepares the mother's body for breastfeeding and facilitates lactation. If a mother is separated from her suckling baby between two consecutive breastfeeding sessions, milk secretion will be reduced.

Milk expressing devices on the market work typically on a single vacuum source which is configured for sucking at a human breast intermittently. This sucking action, though capable of milk expression, is totally different from a baby's suckling. Hence, when a mother has used such a milk expressing device for some time, the amount of expressed milk dwindles. Besides, in order to accelerate milk expression, the sucking pressure is often adjusted to an overly high level, which nevertheless causes pain.

U.S. Pat. No. 6,706,012B2 discloses a milk expressing device with two pressure sources (on the breast shields). While this device can massage the breasts to stimulate milk production, the nipples are deliberately excluded from the massaging areas such that the milk expressing action still differs from a baby's suckling action. Moreover, as a single pump is used as the source of pressure, the two pressure sources on the breast shields are linked in terms of control. This not only limits the variability of control over the breast shields but also makes it difficult to simulate the sensation of being suckled by a baby. In addition, the specifications of the single pump, which is in charge of both pressure sources, must comply with the one pressure source that has the higher flow rate requirement. As a result, the gas pump may be oversized for the other pressure source and prevents further reduction in volume of the device.

Another milk expressing device with multiple pressure sources (on the breast shields) is disclosed in U.S. Pat. No. 7,396,340B2. This device may be able to mimic a baby's suckling action to a certain degree but, owing to its complex structure and high production cost, is not suitable for mass production.

BRIEF SUMMARY OF THE INVENTION

In view of the shortcomings of the prior art, it is an object of the present invention to provide a milk expressing device which can simulate a baby's suckling and which features structural simplicity, high expressing efficiency, and high comfort.

To achieve the above and other objects, the present invention provides a milk expressing device capable of simulating a baby's suckling, wherein the milk expressing device includes a first vacuum source, a second vacuum source, a throttle hole, a solenoid relief valve, a first tube, a second tube, a breast shield, and a control circuit board. The first vacuum source is connected to the breast shield via the first tube. The first tube is provided with the throttle hole to communicate with the atmosphere. When the first vacuum source is turned off, negative pressure in the first tube and in the breast shield disappears slowly through the throttle hole. The second vacuum source is connected to the breast shield via the second tube. The second tube is provided with the solenoid relief valve to communicate with the atmosphere. When the solenoid relief valve is activated, negative pressure in the second tube and in the breast shield can be rapidly removed. The control circuit board is connected to and controls the first vacuum source, the second vacuum source, and the solenoid relief valve.

Preferably, a vacuum tank and a solenoid control valve are provided between the first vacuum source and the first tube, wherein the solenoid control valve is controlled by the control circuit board.

Preferably, the first vacuum source and the second vacuum source are pumps driven by the same motor.

Preferably, the breast shield is composed of a shield body, a liner, and a milk collecting container. The front end of the shield body is a funnel-shaped breast receiving portion for receiving a breast. The liner is a soft resilient member provided between the inner side of the breast receiving portion and the breast received in the breast receiving portion. A second air chamber is formed between the outer side of the liner and the inner side of the breast receiving portion. The inner side of the liner is to be in contact with a breast so that a first air chamber is formed between the inner side of the liner and the breast. The shield body is further provided with a first channel and a second channel. The first channel connects the first air chamber and the milk collecting container and is connected to the first vacuum source via the first tube. The second channel connects the second vacuum source and the second air chamber via the second tube.

Preferably, the liner has three sections: a breast cushion section, a lip simulating section, and a tongue simulating section. The breast cushion section is configured for increasing the comfort of the breast with which the liner is in contact. The stem of a funnel-shaped portion of the liner is recessed radially toward the centerline of the liner to form the lip simulating section. The tongue simulating section is connected to the rear end of the lip simulating section and bulges radially outward.

Preferably, the control circuit board controls the first vacuum source, the second vacuum source, and the solenoid relief valve in three stages. More specifically, the first vacuum source is turned off in stage 1 and stage 3 and is turned on in stage 2. The second vacuum source is turned on in stage 1 and stage 2 and is turned on or off in stage 3. The solenoid relief valve is turned off in stage 1 and stage 2 and is turned on in stage 3. The duration of stage 3 accounts for 40% to 60% of the total duration of the three stages. The duration of stage 2 ranges from 0.08 to 0.25 second.

Preferably, the control circuit board controls the first vacuum source, the solenoid control valve, the second vacuum source, and the solenoid relief valve in three stages. More specifically, the first vacuum source is turned on in stage 1 and stage 3 and is turned on or off in stage 2. The solenoid control valve is turned off in stage 1 and stage 3 and is turned on in stage 2. The second vacuum source is turned on in stage 1 and stage 2 and is turned on or off in stage 3. The solenoid relief valve is turned off in stage 1 and stage 2 and is turned on in stage 3. The duration of stage 3 accounts for 40% to 60% of the total duration of the three stages. The duration of stage 2 ranges from 0.08 to 0.25 second.

The features of the present invention include structural simplicity and high comfort in use. In addition, under the control of the control circuit board, the various components work in conjunction with one another to create the sensation of being suckled by a baby, thus effectively increasing the secretion of milk.

BRIEF DESCRIPTION OF THE SEVERAL VIEWS OF THE DRAWINGS

The structure as well as a preferred mode of use, further objects, and advantages of the present invention will be best understood by referring to the following detailed description of some illustrative embodiments in conjunction with the accompanying drawings, in which.

DETAILED DESCRIPTION OF THE INVENTION

According to studies on babies' suckling behaviors and the related sonograms, a baby's suckling action mainly involves changing the volume in the oral cavity and thereby generating a negative pressure for extracting milk from a breast. Therefore, it is practically impossible for the conventional milk expressing devices, which operate only on a single vacuum source, to precisely simulate the suckling action of a baby's oral cavity. The repeated contraction and expansion of the oral cavity must also be simulated so as for a mother's nipple to feel like being suckled by a baby.

Figure 1:
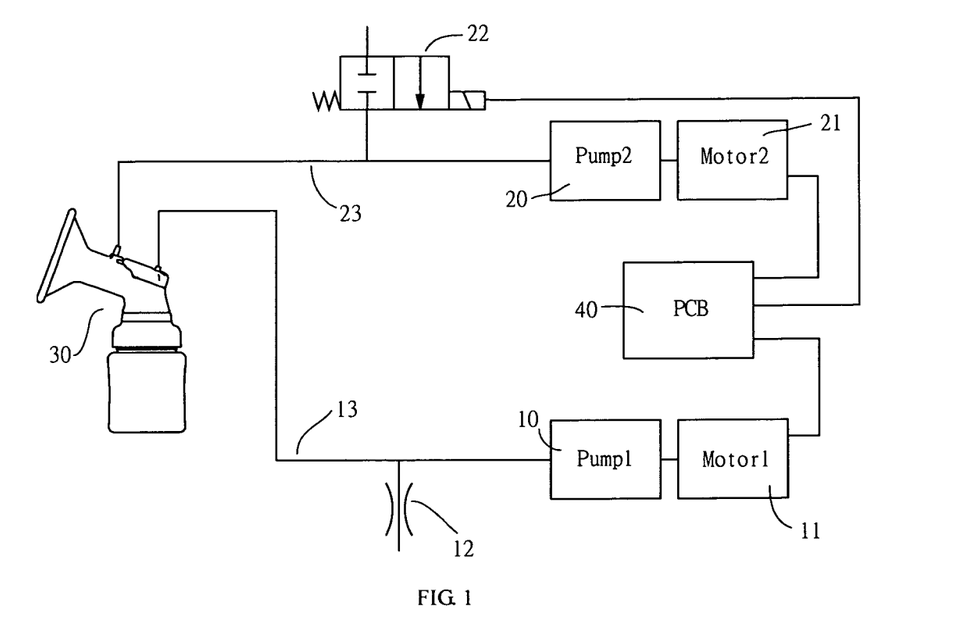
FIG. 1 is a schematic structural diagram of the first embodiment of the present invention.

To this end, the present invention simplifies the contraction and expansion of a baby's oral cavity into two movements: 1. the opening and closing of the mouth, which movement is carried out by lowering and raising the lower jaw to increase and reduce the space in the oral cavity such that a suction force is generated, and the repetition of which movement causes intermittent generation of such a suction force; and 2. swallowing, which movement entails a wavy movement of the tongue to bring the expressed milk down into the esophagus. A baby's suckling action is, in fact, the repetition of a continuous cycle of opening and closing of the mouth and swallowing. When the mouth is opened, negative pressure (i.e., vacuum) is generated in the oral cavity. Once the negative pressure reaches its maximum, the mouth is closed, and swallowing begins. To produce both the sucking action and the repeated contraction and expansion of a baby's oral cavity, an embodiment of the present invention is configured as shown in FIG. 1 and includes a first vacuum source 10, a second vacuum source 20, a throttle hole 12, a solenoid relief valve 22, a first tube 13, a second tube 23, a breast shield 30, and a control circuit board 40. The first vacuum source 10 is driven by a first vacuum source motor 11 and is connected to the breast shield 30 via the first tube 13. The first tube 13 is provided with the throttle hole 12 to communicate with the atmosphere. When the first vacuum source 10 is turned off, negative pressure in the first tube 13 and in the breast shield 30 disappears slowly through the throttle hole 12. The second vacuum source 20 is driven by a second vacuum source motor 21 and is connected to the breast shield 30 via the second tube 23. The second tube 23 is provided with the solenoid relief valve 22 to communicate with the atmosphere. When the solenoid relief valve 22 is activated, the second tube 23 is in communication with the atmosphere to rapidly remove negative pressure from the second tube 23 and from the breast shield 30. The first vacuum source motor 11, the second vacuum source motor 21, and the solenoid relief valve 22 are controlled by the control circuit board 40.

Figure 2:
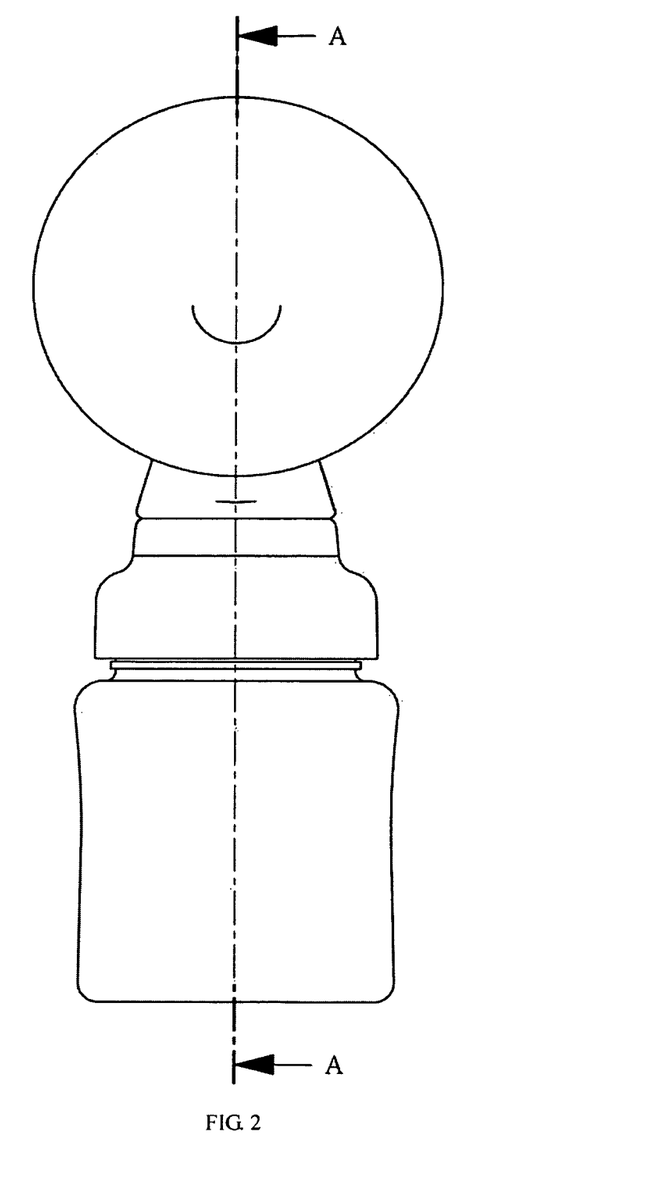
FIG. 2 is a front view of a breast shield.
Figure 3:
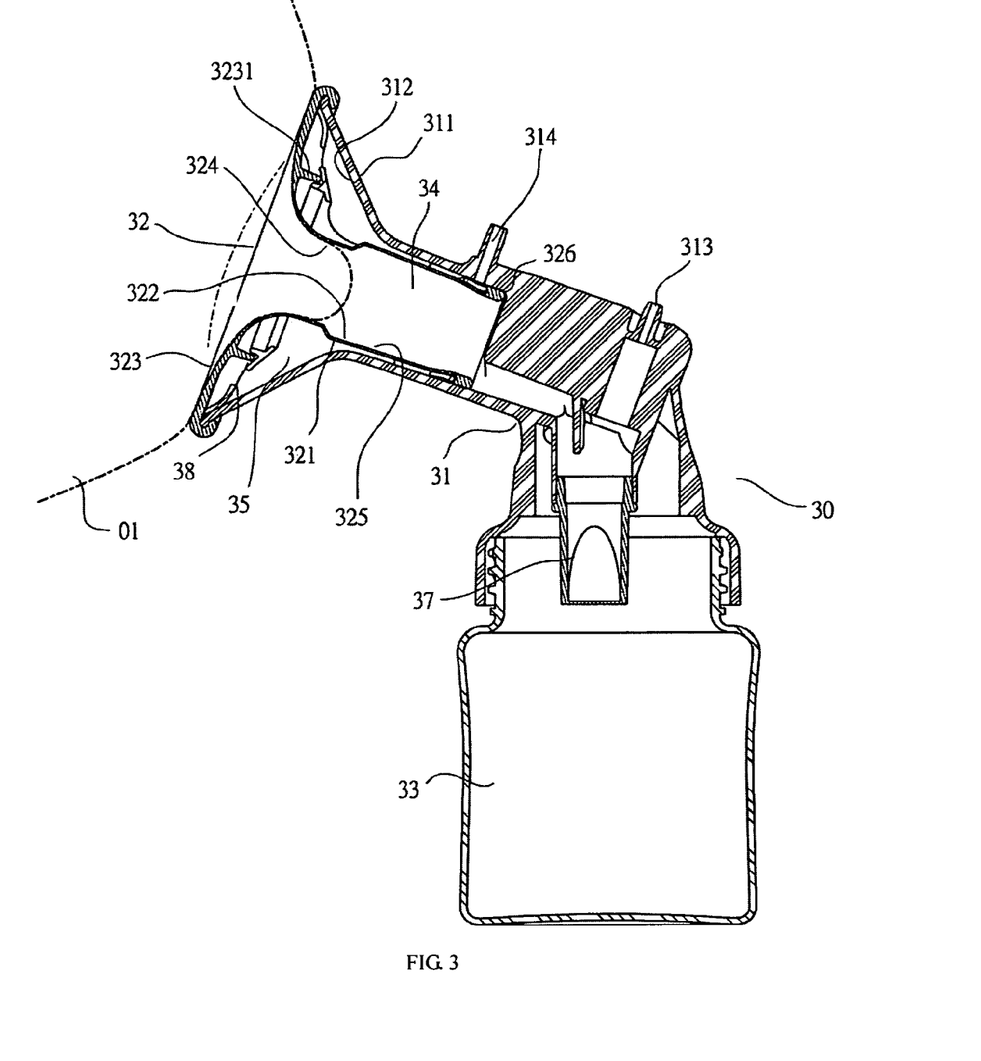
FIG. 3 is the A-A sectional view of the breast shield shown in FIG. 2.
Figure 4:
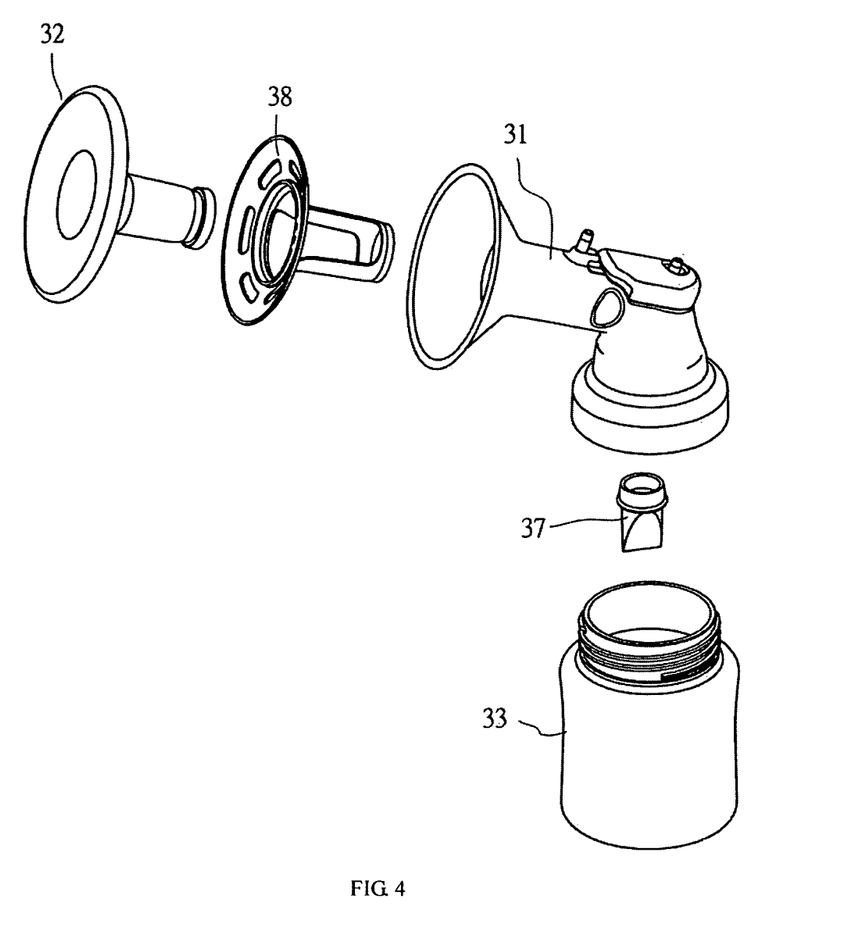
FIG. 4 is an exploded perspective view of the breast shield shown in FIG. 2.

As shown in FIG. 2 to FIG. 4, the breast shield 30 is composed of a shield body 31, a liner 32, and a milk collecting container 33. The shield body 31 has a front end formed as a funnel-shaped breast receiving portion 311 for receiving a breast 01. The liner 32 is a soft resilient member provided between the inner side 312 of the breast receiving portion 311 and the breast 01 received in the breast receiving portion 311. The bottom end 326 of the liner 32 is provided with a gasket fitted tightly in the shield body 31 such that a second air chamber 35 is formed between the outer side 321 of the liner 32 and the inner side 312 of the breast receiving portion 311. The inner side 322 of the liner 32 is to be in contact with the breast 01 so that a first air chamber 34 is formed between the inner side 322 of the liner 32 and the breast 01. The shield body 31 is further provided with a first channel 313 and a second channel 314. The first channel 313 connects the first air chamber 34 and the milk collecting container 33 and is connected to the first vacuum source 10 via the first tube 13. The second channel 314 connects the second vacuum source 20 and the second air chamber 35 via the second tube 23.

To increase the efficiency with which the first vacuum source 10 creates negative pressure, a check valve 37 is optionally provided between the first channel 313 and the milk collecting container 33. By doing so, the space in which the first vacuum source 10 is required to create negative pressure is effectively reduced without affecting the flow of the expressed milk into the milk collecting container 33.

Figure 5:
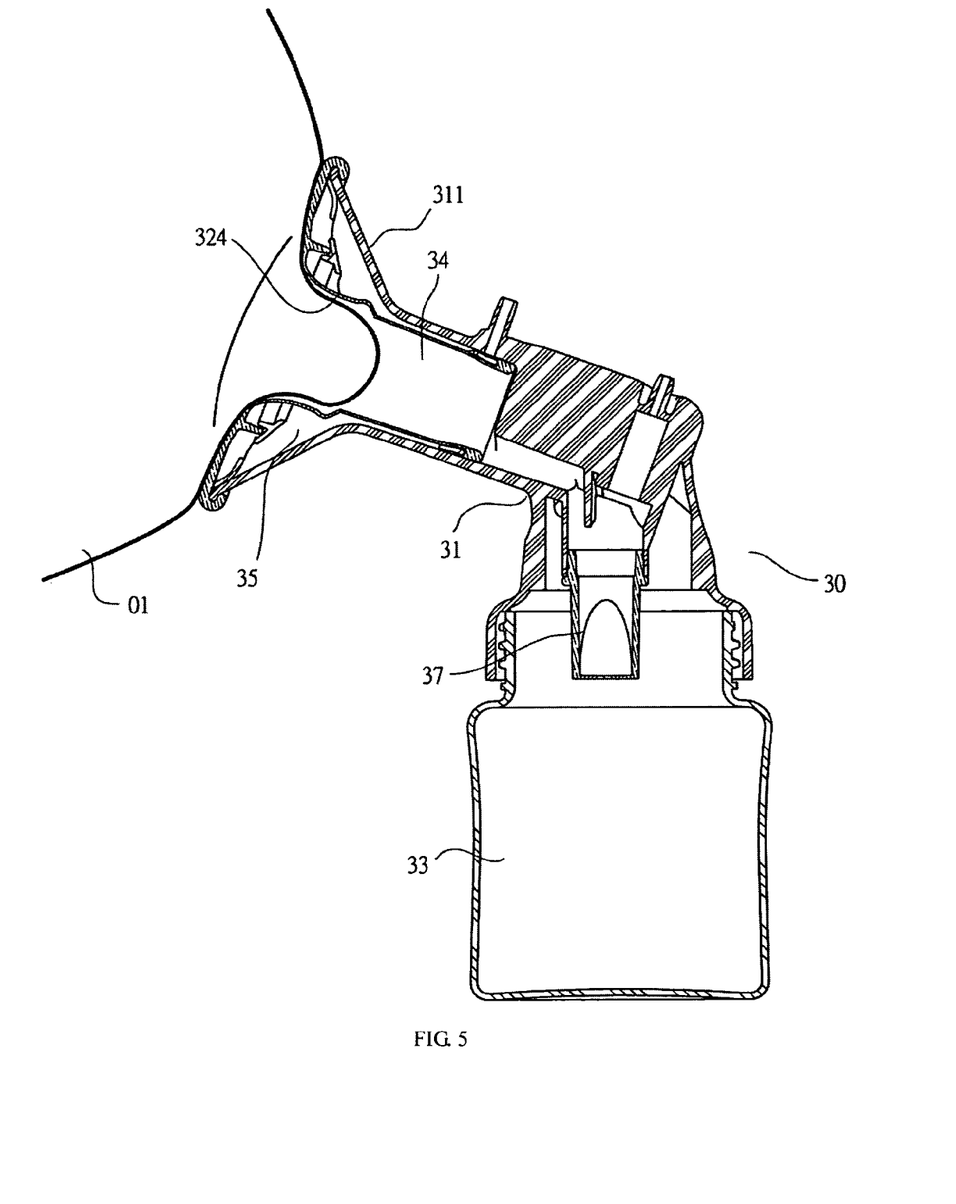
FIG. 5 is the A-A sectional view of the breast shield shown in FIG. 2, with a greater (i.e., more negative) negative pressure in the second air chamber than in the first air chamber.
Figure 6:
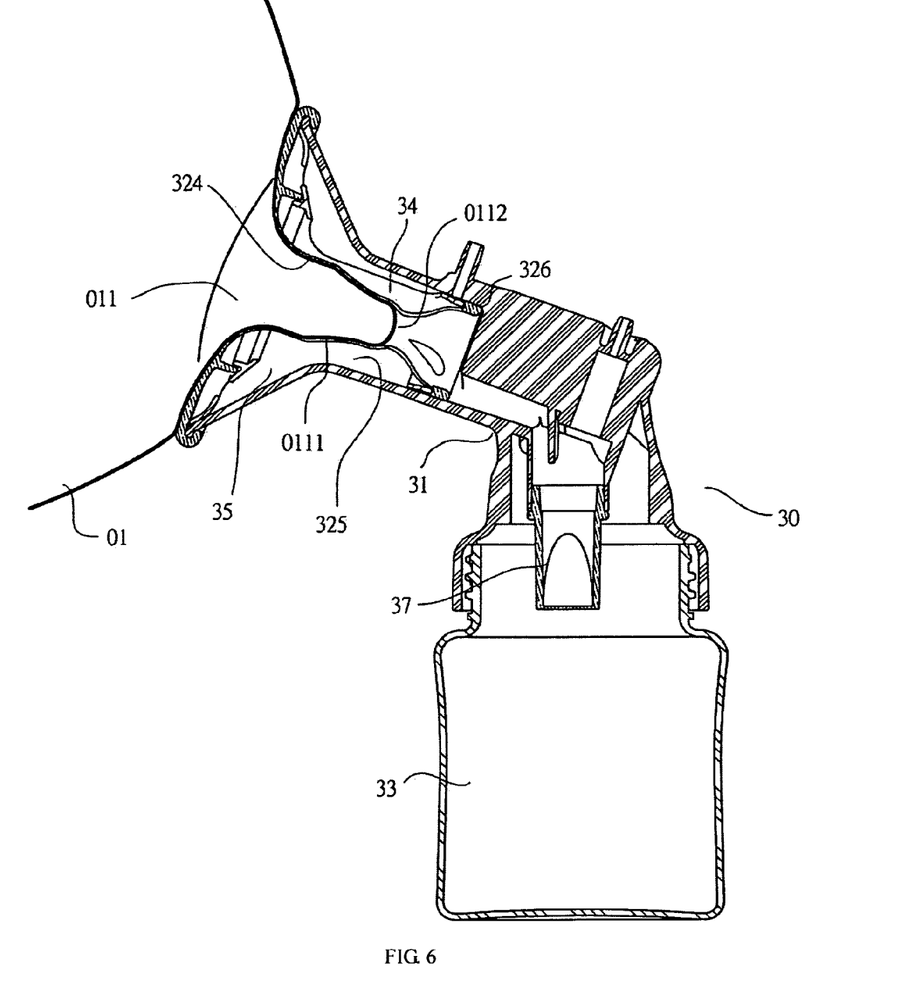
FIG. 6 is the A-A sectional view of the breast shield shown in FIG. 2, with a greater negative pressure in the first air chamber than in the second air chamber.

The liner 32, which is to be in direct contact with the breast 01, includes three sections: a breast cushion section 323, a lip simulating section 324, and a tongue simulating section 325. The breast cushion section 323 is the funnel-shaped portion at the front end of the liner 32 and is provided with a cushion cylinder 3231. With the liner 32 being a soft resilient member, the breast cushion section 323 can increase the comfort of the breast 01 when the breast 01 is in contact with the liner 32. The lip simulating section 324 is the stem of the funnel-shaped portion of the liner 32, and the tongue simulating section 325 is connected to the rear end of the lip simulating section 324. Referring to FIG. 5, when the negative pressure in the second air chamber 35 is greater (i.e., more negative) than that in the first air chamber 34, the lip simulating section 324 moves radially toward the breast receiving portion 311. Consequently, the inner size of the lip simulating section 324 increases to simulate expansion of the oral cavity. When the negative pressure in the first air chamber 34 is greater than that in the second air chamber 35, as shown in FIG. 6, the lip simulating section 324 resumes its original size to simulate contraction of the oral cavity. The tongue simulating section 325 has a radially outwardly bulging shape. When the negative pressure in the first air chamber 34 is greater than that in the second air chamber 35, the tongue simulating section 325 contracts radially and becomes attached to the nipple 011. As the tongue simulating section 325 is long enough to cover the nipple 011 completely, radial contraction of the tongue simulating section 325 causes the tongue simulating section 325 to first attach to the side 0111 of the nipple 011 and then encircle the front end 0112 of the nipple 011, thereby simulating the wavy movement of the tongue. In order to facilitate installation and removal of the liner 32 and further ensure the airtightness of the first air chamber 34 and the second air chamber 35, an additional liner supporting frame 38 is optionally provided to secure the liner 32 in place and prevent the expressed milk from contamination which may otherwise occur if the portion of the liner 32 that is to be in contact with the expressed milk is inadvertently touched during installation of the liner 32. As stated previously, a baby's suckling action is the repetition of a continuous cycle of opening and closing of the mouth and swallowing. In addition, according to sonograms taken of a baby's oral cavity during suckling, the inner space of the oral cavity increases when the baby opens its mouth, thus creating negative pressure (i.e., vacuum) in the oral cavity, and the baby shuts its mouth and swallows simultaneously as soon as the negative pressure peaks. Therefore, negative pressure in the first air chamber 34 and in the second air chamber 35 is controlled in the following sequence:

1. create negative pressure in the second air chamber 35 (in simulation of opening the mouth);
2. create negative pressure in the first air chamber 34 (in simulation of generating negative pressure, or vacuum, in the oral cavity);
3. bring the negative pressure in the first air chamber 34 and in the second air chamber 35 to the maximum at the same time (in simulation of bringing the negative pressure in the oral cavity to the maximum);
4. cause the negative pressure in the second air chamber 35 to disappear (in simulation of shutting the mouth and swallowing); and
5. lower the negative pressure in the first air chamber 34 (in simulation of removing the negative pressure in the oral cavity).

Figure 7:
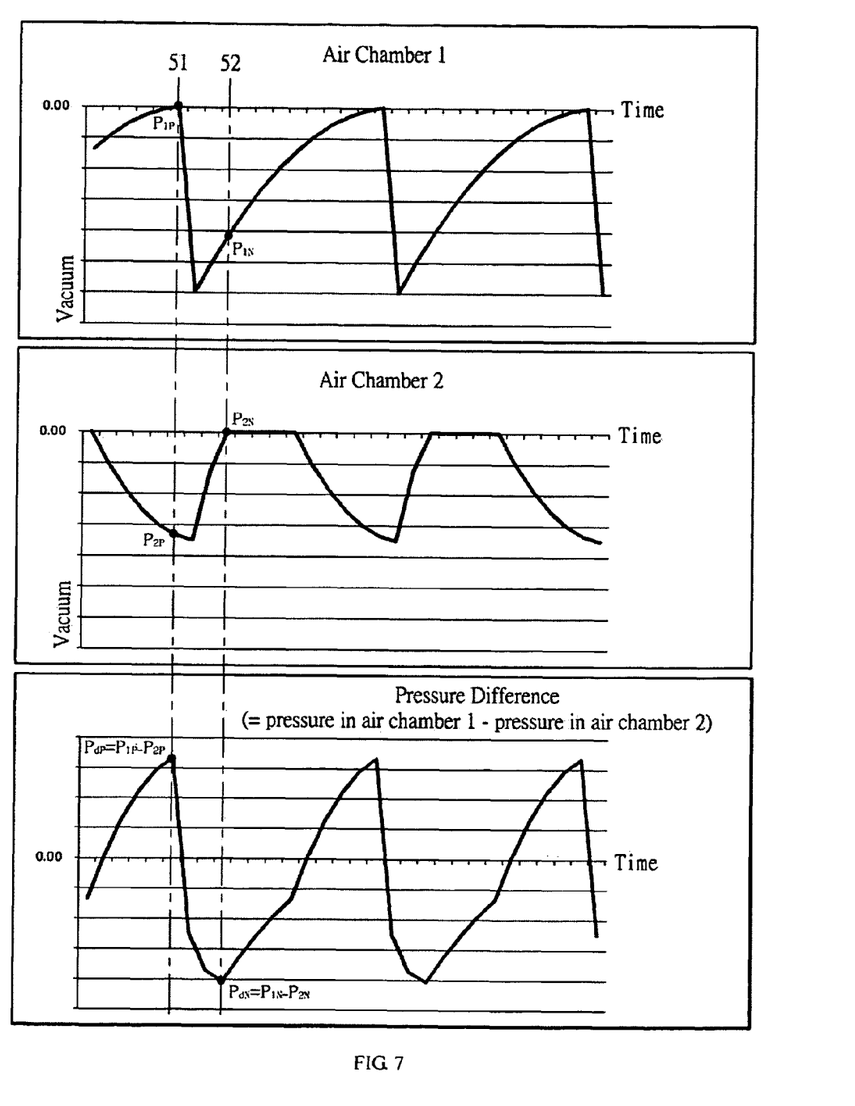
FIG. 7 shows charts plotting the relationships between the negative pressures in the first and the second air chambers and time.

In the foregoing process, the creation of negative pressure in the second air chamber 35 is prior to the creation of negative pressure in the first air chamber 34. However, as simulation of the swallowing action requires that the negative pressure in the first air chamber 34 be greater than that in the second air chamber 35, the negative pressure in the first air chamber 34 must be built up faster than that in the second air chamber 35. On the other hand, in order for the negative pressure in the second air chamber 35 to disappear prior to the lowering of the negative pressure in the first air chamber 34, pressure must release faster from the second air chamber 35 than from the first air chamber 34. In other words, the first vacuum source 10 must have a higher pumping flow rate and a lower relief flow rate than the second vacuum source 20. The aforesaid variations of negative pressure in the air chambers are plotted against time in FIG. 7, in which the variation of the pressure difference basically represents the movements of the lip simulating section 324 and of the tongue simulating section 325 of the liner 32. At the time point 51 in FIG. 7, the pressure difference $P_{dP}$ is a positive value, meaning the negative pressure $P_{2P}$ in the second air chamber 35 is greater (i.e., more negative) than the negative pressure $P_{1P}$ in the first air chamber 34, and this is a simulation of the state in which the mouth is opened. At the time point 52, the pressure difference $P_{dN}$ is a negative value, meaning the negative pressure $P_{2N}$ in the second air chamber 35 is less (i.e., less negative) than the negative pressure $P_{1N}$ in the first air chamber 34, and this is a simulation of the state in which the mouth is shut and swallowing begins.

To perform the above control method, the first vacuum source 10 and the second vacuum source 20 must be vacuum pumps of different flow rates and be driven by different motors respectively. Experiment results also show that, in order to achieve better effects, the flow rate of the first vacuum source 10 must be at least five times as high as that of the second vacuum source 20, wherein the ratio may vary slightly with the ratio of interior space between the first air chamber 34 and the second air chamber 35. In particular, the first vacuum source 10 must have a flow rate not lower than 9 L/min to provide an effective suckling frequency (i.e., 45 to 110 cycles/min). Tabulated below is an example of the control process for generating a suckling frequency of 50 cycles/min, wherein, for optimal effects, the proportion of duration of each stage may require minor adjustment according to the size of space in the first air chamber 34 and in the second air chamber 35 and the space ratio therebetween. Each cycle consists of stage 1, stage 2, and stage 3. The duration of each cycle is the sum of the durations of the three stages and determines the suckling frequency. The duration of stage 3 should take up 40% to 60% of the duration of an entire cycle. The duration of stage 2 should be between 0.08 and 0.25 second.

|  | Stage | | |
| --- | --- | --- | --- |
|  | 1 | 2 | 3 |
| Time sequence | 0 s to 0.5 s | 0.5 s to 0.6 s | 0.6 s to 1.2 s |
| First vacuum source motor (11) | OFF | ON | OFF |
| Second vacuum source motor (21) | ON | ON | ON or OFF |
| Solenoid relief valve (22) | OFF | OFF | ON |

Figure 8:
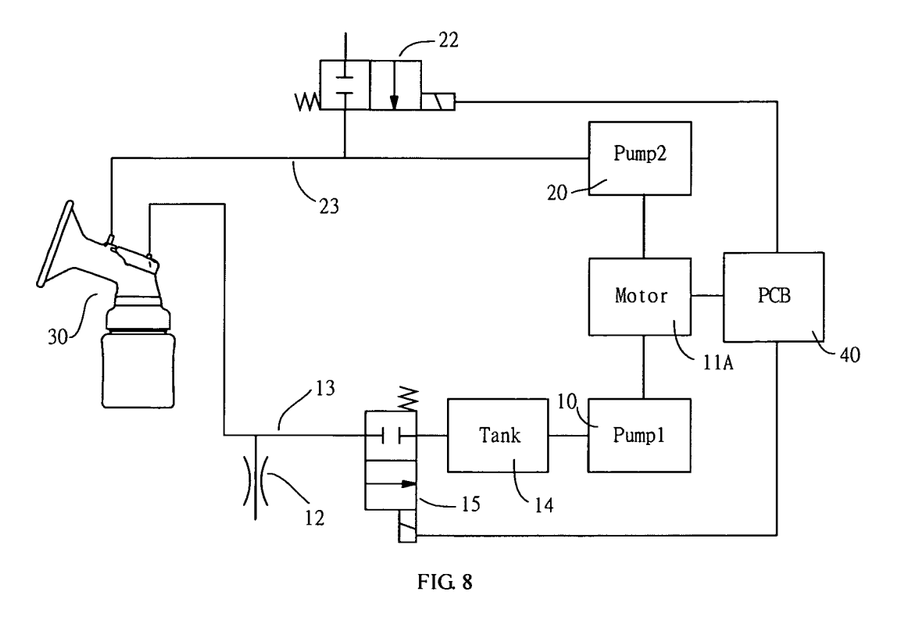
FIG. 8 is a schematic structural diagram of the second embodiment of the present invention.

However, as the high flow-rate first vacuum source 10 required in this embodiment, hereinafter referred to as the first embodiment, is both costly and bulky, and two motors are required for driving the vacuum sources respectively, the resultant milk expressing device leaves much to be desired in terms of cost and physical volume. And this leads to another preferred embodiment of the present invention, as shown in FIG. 8, which is hereinafter referred to as the second embodiment and includes a first vacuum source 10, a second vacuum source 20, a vacuum tank 14, a solenoid control valve 15, a throttle hole 12, a solenoid relief valve 22, a first tube 13, a second tube 23, an breast shield 30, and a control circuit board 40.

In the second embodiment, the first vacuum source 10 is driven by a vacuum source motor 11A and is connected to the vacuum tank 14. The vacuum source motor 11A operates at all times (or substantially at all times) to provide the vacuum tank 14 with sufficient negative pressure. The other outlet of the vacuum tank 14 is provided with the solenoid control valve 15 and is connected to the first channel 313 in the breast shield 30 via the first tube 13. The first tube 13 is provided with the throttle hole 12 to communicate with the atmosphere. When the solenoid control valve 15 is activated, the vacuum tank 14 is in communication with the first tube 13 such that negative pressure is rapidly created in the first tube 13 and in the first air chamber 34 in the breast shield 30. Once the solenoid control valve 15 is turned off, the vacuum tank 14 is blocked from the first tube 13, and the negative pressure in the first tube 13 and in the first air chamber 34 in the breast shield 30 disappears slowly through the throttle hole 12. The second vacuum source 20 is also driven by the vacuum source motor 11A and is connected to the second channel 314 in the breast shield 30 via the second tube 23. The second tube 23 is provided with the solenoid relief valve 22 to communicate with the atmosphere. When the solenoid relief valve 22 is activated, the second tube 23 is in communication with the atmosphere to rapidly remove negative pressure from the second tube 23 and from the second air chamber 35. The vacuum source motor 11A, the solenoid control valve 15, and the solenoid relief valve 22 are controlled by the control circuit board 40.

While the second embodiment has the same effect as the first embodiment, the two vacuum sources in the second embodiment are vacuum pumps of the same specifications, are driven by a single motor, and can be implemented by low flow-rate vacuum pumps (e.g., with a flow rate <3 L/min). Therefore, the volume and cost of the resultant milk expressing device can be substantially reduced as compared with those in the first embodiment. Experiment results show that the intended effect can be achieved with vacuum pumps whose flow rates are 3 L/min, in which case the control process for generating a suckling frequency of 50 cycles/min is tabulated as follows:

|  | Stage | | |
| --- | --- | --- | --- |
|  | 1 | 2 | 3 |
| Time sequence | 0 s to 0.5 s | 0.5 s to 0.6 s | 0.6 s to 1.2 s |
| Vacuum source motor (11A) | ON | ON or OFF | ON |
| Solenoid control valve (15) | OFF | ON | OFF |
| Solenoid relief valve (22) | OFF | OFF | ON |

Figure 9:
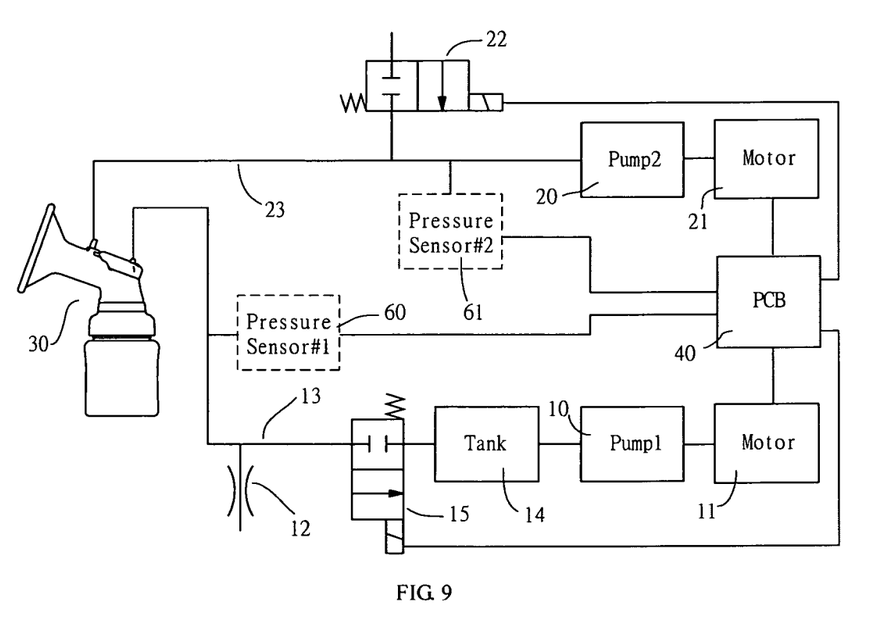
FIG. 9 is a schematic structural diagram of the third embodiment of the present invention.

In practice, the combination of the two vacuum pumps and the single motor in the second embodiment may also be replaced by two independent vacuum pumps, as in the less preferred embodiment shown in FIG. 9. This embodiment, hereinafter referred to as the third embodiment, includes a first vacuum source 10, a second vacuum source 20, a vacuum tank 14, a solenoid control valve 15, a throttle hole 12, a solenoid relief valve 22, a first tube 13, a second tube 23, a breast shield 30, and a control circuit board 40. The first vacuum source 10 is driven by a first vacuum source motor 11 and is connected to the vacuum tank 14. The first vacuum source motor 11 operates at all times (or substantially at all times) to provide the vacuum tank 14 with sufficient negative pressure. The other outlet of the vacuum tank 14 is provided with the solenoid control valve 15 and is connected to the first channel 313 in the breast shield 30 via the first tube 13. The first tube 13 is provided with the throttle hole 12 to communicate with the atmosphere. When the solenoid control valve 15 is activated, the vacuum tank 14 is in communication with the first tube 13 such that negative pressure is rapidly created in the first tube 13 and in the first air chamber 34 in the breast shield 30. Once the solenoid control valve 15 is turned off, the vacuum tank 14 is blocked from the first tube 13, and the negative pressure in the first tube 13 and in the first air chamber 34 in the breast shield 30 disappears slowly through the throttle hole 12. The second vacuum source 20 is driven by a second vacuum source motor 21 and is connected to the second channel 314 in the breast shield 30 via the second tube 23. The second tube 23 is provided with the solenoid relief valve 22 to communicate with the atmosphere. When the solenoid relief valve 22 is activated, the second tube 23 is in communication with the atmosphere to rapidly remove negative pressure from the second tube 23 and from the second air chamber 35 in the breast shield 30. The first vacuum source motor 11, the second vacuum source motor 21, the solenoid control valve 15, and the solenoid relief valve 22 are controlled by the control circuit board 40.

The third embodiment has the same effect as the previous two embodiments. However, as the two vacuum sources in the third embodiment can be implemented by low flow-rate vacuum pumps (e.g., with flow rates <3 L/min), the cost and physical volume of the resultant milk expressing device can be reduced as compared with those in the first embodiment, though slightly increased as compared with those in the second embodiment. Nevertheless, since the first vacuum source 10 and the second vacuum source 20 in the third embodiment are driven by their respective motors, the two vacuum sources are not linked in terms of control, and this allows more flexible and more accurate control over the movements of the various parts of the liner 32 than in the second embodiment, in which the two vacuum sources are driven by a single motor. Experiment results show that the intended effect can be achieved with two vacuum pumps each having a flow rate of 3 L/min, in which case the control process for generating a suckling frequency of 50 cycles/min is as follows:

|  | Stage | | |
| --- | --- | --- | --- |
|  | 1 | 2 | 3 |
| Time sequence | 0 s to 0.5 s | 0.5 s to 0.6 s | 0.6 s to 1.2 s |
| First vacuum source motor (11) | ON | ON or OFF | ON |
| Solenoid control valve (15) | OFF | ON | OFF |
| Second vacuum source motor (21) | ON | ON | ON or OFF |
| Solenoid relief valve (22) | OFF | OFF | ON |

As stated previously, that the first vacuum source 10 and the second vacuum source 20 are independently driven by their respective motors allows the movements of the various parts of the liner 32 to be more flexibly and more accurately controlled. Hence, if it is desired to further increase the accuracy in control, a negative pressure sensor 60 can be provided on the first tube 13, and a negative pressure sensor 61, on the second tube 23. Each pressure sensor produces sensing signals according to pressure level of corresponding tube and chamber. The sensing signals will be sent to the control circuit board 40, so as for the control circuit board 40 to more accurately control the movement of each part of the liner 32 according to the sensing signals.

The embodiments provided herein are only the preferred or less preferred embodiments of the present invention and are not intended to limit the scope of the present invention. All equivalent changes and modifications based on the technical contents disclosed herein should fall within the scope of the present invention.

What is claimed is:
1. A milk expressing device capable of simulating a baby's suckling, comprising: a first vacuum source, a second vacuum source, a throttle hole, a solenoid relief valve, a first tube, a second tube, a breast shield, and a control circuit board, wherein the control circuit board controls the first vacuum source, the second vacuum source, and the solenoid relief valve in three stages, in which: the first vacuum source is turned off in a first stage and in a third stage and is turned on in a second stage, the second vacuum source is turned on in the first stage and in the second stage and is turned on or off in the third stage, and the solenoid relief valve is turned off in the first stage and in the second stage and is turned on in the third stage, the third stage having a duration accounting for 40% to 60% of a total duration of the three stages, the second stage having a duration ranging from 0.08 to 0.25 second.

2. The milk expressing device of claim 1, further comprising a vacuum tank and a solenoid control valve, both provided between the first vacuum source and the first tube, wherein the solenoid control valve is controlled by the control circuit board.

* * * * *